United States Patent [19]

Aoyagi

[11] Patent Number: 5,504,002
[45] Date of Patent: Apr. 2, 1996

[54] CRYOPRESERVING BOVINE EMBRYOS WITH A COMPOSITION COMPRISING 4
[54] ETHYLEN E GLYCOL, 4
[54] PROPANEDIOL, AND BOVINE ALBUMIN HAVING A LIPID CONTENT OF 2.5 UG OR MORE

[75] Inventor: Yoshito Aoyagi, Tsuchiura, Japan

[73] Assignee: National Federation of Agricultural Cooperative Associations, Tokyo, Japan

[21] Appl. No.: 181,217

[22] Filed: Feb. 3, 1994

[30] Foreign Application Priority Data

Apr. 6, 1993 [JP] Japan .................... 5-078447

[51] Int. Cl.$^6$ .............. A01N 1/02; C12N 5/00; A61B 17/43; A61D 7/00
[52] U.S. Cl. ............ 435/240.2; 435/1.3; 435/2; 600/33; 600/34; 600/35
[58] Field of Search ................ 435/1, 2, 240.2; 600/33, 34, 35

[56] References Cited

U.S. PATENT DOCUMENTS

| | | | |
|---|---|---|---|
| 4,186,253 | 1/1980 | Yokogama et al. | 435/240 |
| 4,931,361 | 6/1990 | Baldeschwieler et al. | 428/402.2 |
| 5,001,047 | 3/1991 | Liberman | 435/1 |
| 5,096,822 | 3/1992 | Rosenkrans, Jr. et al. | 435/240.1 |
| 5,102,783 | 4/1992 | Alkemade et al. | 435/1 |
| 5,160,312 | 11/1992 | Voelkel | 600/34 |

FOREIGN PATENT DOCUMENTS 63-33867  7/1988  Japan .

WO91/12719  9/1991  WIPO .

OTHER PUBLICATIONS

Sigma Chemical Co., "Biochemicals Organic Compounds", 1990, pp. Alphabetical List of Compounds.
Australian Office Action.
O. Dochi et al., "Study on direct transfer methods of bovine frozen embryo", Abstract of Bulletin of Hokkaido Bovine Fertilized Ova Transfer Society, No. 10, 36–40, 1991.
Y. Aoyagi et al., "Effects of sucrose dilution on survival rate of frozen–thawed bovine embryo . . . ". Abstract of Bulletin of Hokkaido Bovine Fertilized Ova Transfer Society, No. 11, 19–21, 1992.
K. Goto et al., "Non-step methods of bovine in vitro fertilization embroyo", Abstract of Journal of Reproduction and Development, vol. 38, No. 5, 1992.
Y. Aoyagi et al., "Effects of Interval to Seeding & Temperatured to Removing Glycerol on Conception of Frozen Embryo of Holstein Cows", Jpn. J. Anim. Reprod., vol. 36(4), 245–248, 1990.

*Primary Examiner*—Marian C. Knode
*Assistant Examiner*—Deborah K. Ware
*Attorney, Agent, or Firm*—Foley & Lardner

[57] ABSTRACT

A method for freezing bovine embryos with a composition which includes 4% ethylene glycol and 4% propanediol and in addition 4% bovine serum albumin containing a high lipid content is disclosed. The mixture is subjected to freezing and used in a method for reproducing cattle by transferring to a cow recipient directly after thawing the preserved embryos. Further, a high lipid content is disclosed as 2.5 ug or more of lipid/mg of bovine serum albumin. The bovine embryos are obtained by in vivo fertilization or by in vitro fertilization for use in the disclosed methods.

4 Claims, 1 Drawing Sheet

CRYOPRESERVING BOVINE EMBRYOS WITH A COMPOSITION COMPRISING 4% ETHYLEN E GLYCOL, 4% PROPANEDIOL, AND BOVINE ALBUMIN HAVING A LIPID CONTENT OF 2.5 UG OR MORE

BACKGROUND OF THE INVENTION

The present invention relates to a method for cryopreserving bovine embryos. The present invention relates also to a method for reproducing cattle in which the cryopreserved embryo can be transferred to recipients directly without testing the embryo.

DESCRIPTION OF THE PRIOR ART

In the reproductive field of cattle breeding, the transfer of embryo has been widely employed as a practical technique. A method for freezing a bovine embryo generally comprises selection of embryo, immersion of the embryo in a cryoprotectant and their equilibration with the cryoprotectant, enclosure in a straw for cryopreservation, cooling, ice seeding, and long-term preserving in liquid nitrogen. The transfer of frozen embryo to cattle requires thawing in air for several seconds, additionally thawing in warm water, removal of the cryoprotectant, and transfer into recipients.

As a method for freezing a bovine embryo, a step-wise method is a leading method in the world. The step-wise method comprises diluting and removing step-wise glycerol added as cryoprotectant by the use of a sucrose solution, confirming the survival of embryos, sucking the embryo into a straw, and then transferring them to recipients. The present inventor examined this method by using embryos obtained by in vivo fertilization. As a result, 98% of thawed embryos survived, and a conception rate of 59% (65/110) could be attained by one-embryo transfer (Aoyagi Y. et al., Jpn. J. Anim. Reprod., 36, 245–248 (1990)).

However, when this method was examined using bovine embryos obtained by in vitro fertilization, the percentage of embryos surviving after freezing and thawing was 47%, namely, the method was found to be of little practical use. The present inventor attempted a method in which after the removal of glycerol, sucrose was removed stepwise for lessening osmotic shock, whereby the survival rate was increased up to 77%. When bovine embryos obtained by in vitro fertilization which had been frozen and then thawed were subjected to two-embryo transfer to recipients according to this method, a conception rate of 53% (30/57) could be attained. In a control group in which the stepwise removal of sucrose was carried out, a conception rate attained by two-embryo transfer of bovine embryos obtained by in vivo fertilization which had been frozen and then thawed was 77% (17/22). Thus, there was a significant difference in conception rate between the in vitro embryo group and the control (in vivo) group (Aoyagi Y. et al., "Hokkaido Usi Juseiran Ishoku Kenkyukai Kaiho (Bulletin of Hokkaido Bovine Embryo Transfer Society)" No. 11, 19–21 (1992)).

For these reasons, it is pointed out that the step-wise method using glycerol as a cryoprotectant involves few problems in the case of using embryos obtained by in vivo fertilization but involves many problems in the case of using embryos subjected to artificial operations such as in vitro fertilization. Therefore, there has been a desire to seek further improvement in a cryoprotectant for further increasing the survival rate after thawing.

In addition, when embryos are taken out of a frozen-embryo containing straw prepared by a conventional step-wise method using glycerol and transferred to recipients, the removal of glycerol from surviving embryos is troublesome. According to the method of the present invention, this troublesome step can be overcome.

On the other hand, a method for transfer by direct thawing of frozen embryos (Leibo S. P., Theriogenology, 21, 767–790 (1984); Suzuki T., Japanese Patent Kokoku No. 63-33867; Massip A. and Van Der Zwalmen P., Vet. Rec., 115, 327–328 (1984); Massip A et al., Theriogenology, 27, 69–79 (1987)) has been reported as a method in which like frozen semen, frozen embryos can be immediately transferred to recipients from a straw after thawing. But, in this case, the conception rate after thawing is as very low as about 30–50%. Thereafter, it has been reported that as substitutes for glycerol, propanediol (Goto K. et al., Jpn. J. Anim. Reprod., 38, 15–18 (1992)) and ethylene glycol (Dochi O. et al., "Bulletin of Hokkaido Bovine Embryo Transfer Society" No. 10, 36–40 (1991) are effective as cryoprotectants, and that when these compounds are used, conception can be achieved by direct transfer into uterus without dilution of the compounds. However, when these compounds are used, only unstable results can be obtained with respect to the survival rate after freezing and thawing and the conception rate, namely, the compounds do not have a larger cryoprotective effect than does glycerol.

When glycerol is used as a cryoprotectant, the survival rate after freezing and thawing of embryos subjected to external treatment for a long period of time (for example, embryos obtained by in vitro fertilization, embryos in an advanced developmental stage obtained by external cultivation of embryos of low quality obtained by in vivo fertilization, embryos from which some cells have been removed for biopsy, and embryos subjected to nuclear transplantation) is low, and their direct transfer after thawing is difficult. When ethylene glycol, propanediol or the like is used alone in place of glycerol, the survival rate after freezing and thawing is not higher than when glycerol is used.

SUMMARY OF THE INVENTION

From a new viewpoint, the present inventor found a method in which when bovine serum albumin (hereinafter abbreviated as BSA) containing a large amount of lipids which are considered to be the main constituents of cell membrane is added to a conventional cryoprotectant to a high concentration, the survival rate after freezing and thawing can be greatly improved and these embryos can be directly transferred to recipients without selecting them individually. It can be conjectured that the lipid components have some cryoprotective effect on the cell membrane of embryos directly or indirectly in cooperation with the cryoprotectant. However, the above reason for the improved survival rate of bovine frozen embryos is based on speculations and does not affect on the establishment of the present invention.

The cryoprotectant usable in the method of the present invention includes, for example, ethylene glycol, propanediol and glycerol, but is not limited to them. These compounds may be used singly or in combination of two or more thereof.

DESCRIPTION OF THE PREFERRED EMBODIMENTS

The present invention is illustrated in detail with the following examples.

EXAMPLE 1

The following test was carried out for investigating the survival rate after freezing and thawing.

1. Experimental method (1) Embryos:

seven-day-old embryos obtained by in vitro fertilization of Japanese Black Cattle, at a developmental stage of blastocyst (quality rank: 1 or 2).

(2) Cryoprotectant:

① 10% glycerol (phosphate buffer (PBS)+0.4% bovine serum albumin (BSA))

② 10% ethylene glycol (PBS+0.4% BSA)

③ 10% propanediol (PBS+0.4% BSA)

④ 4% ethylene glycol+4% propanediol (PBS+0.4% BSA)

⑤ 4% ethylene glycol+4% propanediol (PBS+4% BSA)

⑥ 4% ethylene glycol+4% propanediol (PBS+0.4% BSA including a high lipid content)

⑦ 4% ethylene glycol+4% propanediol (PBS+4% BSA including a high lipid content)

Groups of embryos treated with the above seven combinations, respectively, were compared in survival rate after freezing and thawing. ALUBUMIN BOVINE FRACTION V A-8022 of Sigma Chemical Co. was used as BSA, and ALUBUMIN™ I of Gibco was used as BSA including a high lipid content (2.5 μg/mg or more).

(3) Sugar solution:

0.3M sucrose (PBS+0.4% BSA)

(4) Container for freezing:

a 0.25-ml plastic straw (5) Method for insertion into the straw:

As shown in FIG. 1, the following were inserted so as to be located in the numerical order from the cotton plug end in the straw:

① the sugar solution (0.3M sucrose)

② air

③ the cryoprotectant and embryo

④ air

⑤ the sugar solution (0.3M sucrose)

(6) Program freezer:

Procool bath mfd. by Tokyo Rika (7) Ice seeding temperature: −6° C.

(8) Cooling rate: 0.5° C./min (9) Temperature at the immersion of liquid nitrogen: −32.5° C.

(10) Thawing method:

The straw was taken out of liquid nitrogen, held in air (at room temperature) for 5 to 10 seconds, and then thawed in warm water at 35° C.

(11) Method for recovering the contents of the straw:

The whole contents of the straw were taken out and placed in an empty plastic Petri dish to be made into drops.

(12) Washing and cultivation of recovered embryos:

The aforesaid drops were diluted with a culture medium (CRlaa medium+5% calf serum) so as to increase the volume gradually to a final volume of 3 ml over a period of about 5 minutes. Thereafter, the thawed embryos were washed with CRlaa medium+5% calf serum and then cultured for 48 hours, after which the survival rate was investigated.

2. Results

TABLE 1

| Cryopratectant | Survival rate after cultivation | Hatchability after cultivation |
|---|---|---|
| Group 1 | 77% (26/34) | 47% (16/34) |
| Group 2 | 74% (23/31) | 45% (14/31) |
| Group 3 | 52% (23/44) | 23% (10/44) |
| Group 4 | 80% (28/35) | 40% (14/35) |
| Group 5 | 82% (27/33) | 36% (12/33) |
| Group 6 | 86% (30/35) | 43% (15/35) |
| Group 7 | 100% (34/34) | 71% (24/34) |

3. Consideration

A high survival rate of 100% could be attained in group 7 (the group treated with 4% BSA including a high lipid content). The hatchability from zona pellucida in group 7 was as high as 71%. There was a significant difference ($P<0.05$) in hatchability from zona pellucida between group 7 and the other groups. That is, BSA including a high lipid content was proved to have some cryoprotective effect.

EXAMPLE 2 (TRANSPLANTATION AND CONCEPTION TEST)

1. Experimental method

A group treated by a step-wise method using 10% glycerol was used as a control group. Embryos frozen and then thawed in the same manner as in group 7 in Example 1 were non-surgically transferred to uterus horn on the corpus luteum side of recipients. The seven-day-old embryos used were those of rank 1 or 2 (embryos obtained by in vivo fertilization or in vitro fertilization) of Japanese Black Cattle. Pregnancy diagnosis was carried out by rectal palpation or ultrasonic diagnosis 60 days or more after the estrus day before the transfer.

2. Results

TABLE 2

| Method | Number of embryos thawed | Number of embryos discarded | Conception rate |
|---|---|---|---|
| SW*. one-embryo (in vivo) transplantation | 115 | 5 (4%) | 59% (65/110) |
| SW*. two-embryo (in vitro) transplantation | 148 | 34 (23%) | 53% (30/57) |
| Group 7** one-embryo (in vivo) transplantation | 38 | 0 (0%) | 63% (24/38) |
| Group 7** one-embryo (in vitro) transplantation | 24 | 0 (0%) | 54% (13/24) |

*SW: step-wise method.
**group 7: freezing and thawing in the same manner as in group 7 in Table 1, followed by transfer to recipients without embryo testing.

3. Consideration

When freezing was carried out according to the method of the present invention, the discard rate was 0% for both the embryos obtained by in vivo fertilization and the embryos obtained by in vitro fertilization, and it was found that the simpler and direct transfer gives a conception rate which is by no means lower than that attained by two-embryo transfer by the step-wise method.

BRIEF DESCRIPTION OF THE DRAWINGS

There is given a cross-sectional view of a straw enclosing an embryo according to the present invention.

In the accompanying drawings:

Figure 1:
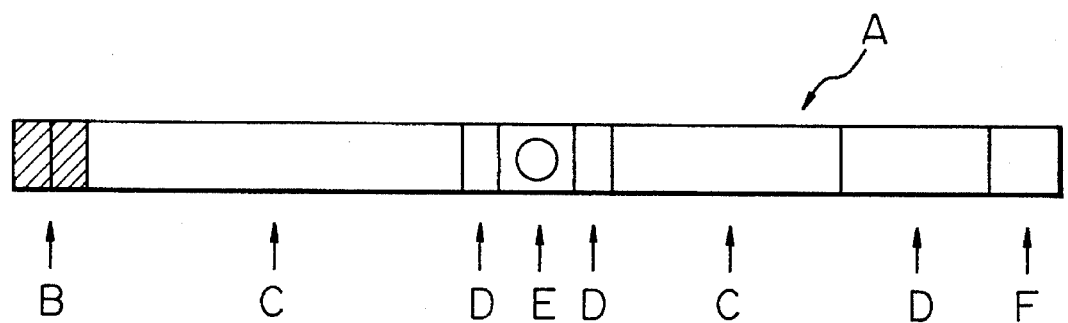

A main body of straw,
B cotton plug,
C sugar solution,
D air,
E cryoprotectant+embryo,
F seal.

What is claimed is:

1. A method for freezing bovine embryos which comprises mixing a bovine embryo with a composition comprising a cryoprotectant comprising 4% ethylene glycol and 4% propanediol, said composition further comprising 4% bovine serum albumin which contains at least 2.5 ug of lipid/mg of bovine serum albumin, and then freezing the resulting mixture.

2. A method for reproducing cattle which comprises cryopreserving bovine embryos in a composition comprising a cryoprotectant comprising 4% ethylene glycol and 4% propanediol, said composition further comprising 4% bovine serum albumin which contains at least 2.5 ug of lipid/mg of bovine serum albumin, thawing the preserved embryos, and then transferring the thawed embryos directly to recipients.

3. A method according to claim 1, wherein the bovine embryos are those obtained by in vivo fertilization or by in vitro fertilization.

4. A method according to claim 2, wherein the bovine embryos are those obtained by in vivo fertilization or by in vitro fertilization.

* * * * *

UNITED STATES PATENT AND TRADEMARK OFFICE
CERTIFICATE OF CORRECTION

PATENT NO.  : 5,504,002
DATED       : April 2, 1996
INVENTOR(S) : Yoshito Aoyagi It is certified that error appears in the above-indentified patent and that said Letters Patent is hereby corrected as shown below:

```
Title page, item [54] and col. 1, line 3, in the Title, should read--
wherin "4 ETHYLENE E GLYCOL, $" should read --4% ETHYLENE GLYCOL, 4%--.

Item [21], change the erial number from "181,217" to -- 191,217--.
```

Signed and Sealed this

Twenty-seventh Day of August, 1996

Attest:

BRUCE LEHMAN

*Attesting Officer*   *Commissioner of Patents and Trademarks*